United States Patent [19]

Westwood et al.

[11] 4,350,695
[45] Sep. 21, 1982

[54] ANTIHISTAMINIC AND BRONCHOSPASMOLYTIC TRIAZOLOQUINAZOLINONES

[75] Inventors: Robert Westwood, Faringdon; Wilfred R. Tully, Cirencester; Robert Murdoch, Highworth, all of Great Britain

[73] Assignee: Roussel Uclaf, Paris, France

[21] Appl. No.: 234,544

[22] Filed: Feb. 13, 1981

[30] Foreign Application Priority Data

Feb. 14, 1980 [GB] United Kingdom ............. 8005089

[51] Int. Cl.³ .................. A61K 31/505; C07D 487/04
[52] U.S. Cl. ............................. 424/251; 424/248.57; 544/251; 544/115; 544/287
[58] Field of Search .............. 544/251, 115; 424/251, 424/248.57

[56] References Cited

U.S. PATENT DOCUMENTS 3,850,932 11/1974 Kathawala .................... 544/251

FOREIGN PATENT DOCUMENTS 2757929 7/1979 Fed. Rep. of Germany ...... 544/251
578314 10/1977 U.S.S.R. ........................... 424/251

OTHER PUBLICATIONS

Bowie, et al., Chemical Abstracts, vol. 92, 128148w (1980), J. Chem. Soc., Perkin Trans., 2/79 (12), pp. 1708-1714.

Primary Examiner—Robert Gerstl
Assistant Examiner—Diana G. Rivers
Attorney, Agent, or Firm—Hammond & Littell, Weissenberger and Muserlian

[57] ABSTRACT

Novel triazoloquinazolinones of the formula

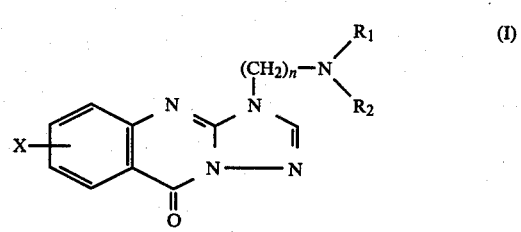

wherein X is selected from the group consisting of hydrogen, halogen, $-NO_2$, methyl, methoxy and $-CF_3$, n is an integer from 2 to 5, $R_1$ and $R_2$ are individually selected from the group consisting of hydrogen and alkyl and hydroxyalkyl of 1 to 5 carbon atoms and taken together with the nitrogen atom to which they are attached form a saturated heterocycle optionally containing another heteroatom and optionally substituted with at least one member of the group consisting of hydroxy, alkyl and hydroxyalkyl of 1 to 5 carbon atoms, cycloalkyl of 3 to 6 carbon atoms, acyl of an aliphatic carboxylic acid of 1 to 5 carbon atoms, alkoxycarbonyl of 2 to 6 carbon atoms and aryl optionally substituted with a halogen or $-CF_3$ and their non-toxic, pharmaceutically acceptable acid addition salts having antihistaminic and bronchospasmolytic activity and their preparation.

23 Claims, No Drawings

ANTIHISTAMINIC AND BRONCHOSPASMOLYTIC TRIAZOLOQUINAZOLINONES

OBJECTS OF THE INVENTION

It is an object of the invention to provide the novel triazoloquinazolinones of formula I and their non-toxic, pharmaceutically acceptable acid addition salts and a process for their preparation and novel intermediates therefore.

It is another object of the invention to provide novel antihistaminic and bronchospasmolytic compositions and to a novel method of treating histaminic conditions and bronchospasms in warm-blooded animals.

These and other objects and advantages of the invention will become obvious from the following detailed description.

THE INVENTION

The novel compounds of the invention are selected from the group consisting of triazoloquinazolinones of the formula

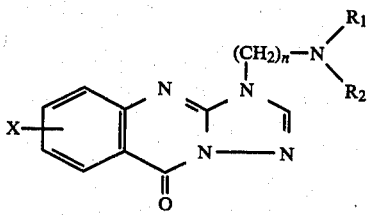

wherein X is selected from the group consisting of hydrogen, halogen, $-NO_2$, methyl, methoxy and $-CF_3$, n is an integer from 2 to 5, $R_1$ and $R_2$ are individually selected from the group consisting of hydrogen and alkyl and hydroxyalkyl of 1 to 5 carbon atoms and taken together with the nitrogen atom to which they are attached form a saturated heterocycle optionally containing another heteroatom and optionally substituted with at least one member of the group consisting of hydroxy, alkyl and hydroxyalkyl of 1 to 5 carbon atoms, cycloalkyl of 3 to 6 carbon atoms, acyl of an aliphatic carboxylic acid of 1 to 5 carbon atoms, alkoxycarbonyl of 2 to 6 carbon atoms and aryl optionally substituted with a halogen or $-CF_3$ and their non-toxic, pharmaceutically acceptable acid addition salts.

Examples of suitable halogens of X are flourine, chlorine and bromine. Examples of $R_1$ and $R_2$ are hydrogen, alkyl of 1 to 5 carbon atoms such as methyl, ethyl, propyl, isopropyl, butyl, isobutyl, tert.-butyl and pentyl; and hydroxyalkyl of 1 to 5 carbon atoms such as hydroxypropyl, hydroxybutyl, hydroxypentyl and especially hydroxyethyl. Examples of suitable saturated heterocycle of

are pyrrolidino, piperidino, morpholino and piperazino, each of which may be substituted with at least one member of the group consisting of hydroxy; alkyl of 1 to 5 carbon atoms such as methyl and ethyl; hydroxyalkyl of 1 to 5 carbon atoms such as hydroxyethyl; cycloalkyl of 3 to 6 carbon atoms such as cyclopropyl and cyclohexyl; formyl, acetyl, carbamoyl, thiocarbamoyl, mono- or dialkylcarbamoyl or thiocarbamoyl of 1 to 5 alkyl carbon atoms and alkylsulfonyl with 1 to 6 alkyl carbon atoms, alkoxycarbonyl of 2 to 6 carbon atoms such as methoxycarbonyl, ethoxycarbonyl, propoxycarbonyl, butoxycarbonyl and isobutoxycarbonyl and aryl such as phenyl.

Examples of suitable acids for the formation of the non-toxic, pharmaceutically acceptable acid addition salts are mineral acids such as hydrochloric acid, hydrobromic acid, hydriodic acid, nitric acid, sulfuric acid and phosphoric acid, and organic acids such as acetic acid, formic acid, propionic acid, maleic acid, fumaric acid, succinic acid, tartaric acid, citric acid, oxalic acid, glyoxylic acid or aspartic acid, alkanesulfonic acids such as methanesulfonic acid or ethanesulfonic acid, arylsulfonic acids, such as benzenesulfonic acid or p-toluenesulfonic acid or arylcarboxylic acids, such as benzoic acid. Such acid addition salts may contain more than one acid moiety and, for example, dihydrochlorides may be obtained.

Among the preferred compounds of formula I are those wherein X is hydrogen, methyl or nitro, those wherein n is 3, 4 or 5 and those wherein

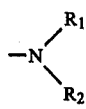

form a saturated heterocycle containing another heteroatom and optionally substituted with at least one member of the group consisting of hydroxy, cycloalkyl of 3 to 6 carbon atoms, alkoxycarbonyl of 2 to 6 carbon atoms, phenyl and halophenyl. Especially preferred compounds are wherein X is hydrogen or methyl and

form a 4-phenylpiperazin-1-yl, 4-(chlorophenyl)-piperazin-1-yl or 4-(ethoxycarbonyl)-piperazin-1-yl radical.

Particularly preferred compounds of the invention are 1-{4-[4-(m-chlorophenyl)-piperazin-1-yl]-butyl}-[1,2,4]-triazolo-[5,1-b]-quinazolin-5-(1H)-one, 1-{4-[4-(ethoxycarbonyl)-piperazin-1-yl]-butyl}-[1,2,4]-triazolo-[5,1-b]-quinazolin-5-(1H)-one, 1-{4-[4-(ethoxycarbonyl)-piperazin-1-yl]-butyl}-7-methyl-[1,2,4]-triazolo-[5,1-b]-quinazolin-5(1H)-one, 1-{3-[4-(ethoxycarbonyl)-piperazin-1-yl]-propyl}-7-methyl-[1,2,4]-triazolo-[5,1-b]-quinazolin-5-(1H)-one and their non-toxic, pharmaceutically acceptable acid addition salts, especially their dihydrochloride.

The novel process of the invention for the preparation of the compounds of formula I comprises reacting a compound of the formula

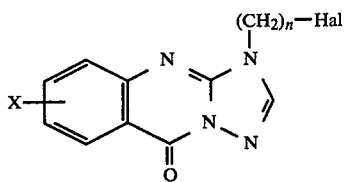

(II)

wherein X and n have the above definitions and Hal is chlorine, bromine or iodine with an amine of the formula

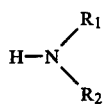

III.

wherein $R_1$ and $R_2$ have the above definition to form the corresponding compound of formula I which may be salified with approximately stoichiometric amounts of an acid, if desired, to form the acid addition salt.

Preferably, the compounds of formulae II and III are reacted by heating such as at about 110° C. for about 10 to 15 hours in an inert organic solvent such as dimethylformamide, preferably in the presence of a condensation agent such as pyridine or triethylamine.

The compounds of formula II are novel compounds and may be prepared by reacting a compound of the formula

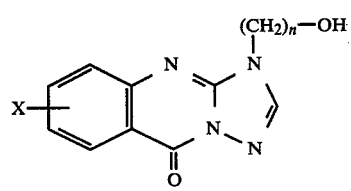

(IV)

wherein X and n have the above definitions with a halogenating agent. Preferably, X is hydrogen, halogen, —CF₃, methyl or methoxy and the preferred halogenating agents are thionyl chloride or a phosphorus halide. The reaction is preferably effected at reflux in an inert organic solvent such as halogenated hydrocarbons like dichloroethane or an ether such as tetrahydrofuran.

The compounds of formula IV are novel also and may be prepared by reacting a compound of the formula

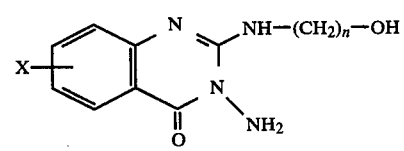

(V)

wherein X and n have the above definition with a formylating agent whereby the corresponding compound of formula IV is obtained. A preferred formylating agent is dimethylacetal or diethylacetal of dimethylformamide preferably used in the presence of a hydrocarbon solvent such as toluene and preferably at reflux. An acid agent such as p-toluenesulfonic acid is also desirably present.

Other formylating agents which can be used include trimethyl orthoformate, triethyl orthoformate, formic acid and dimethylformamide in conjunction with a suitable acid chloride e.g. benzoyl chloride. However, care must be taken to avoid side reactions with the side chain alcohol group.

The compounds of formula V are also novel compounds and may be prepared by reacting a compound of the formula

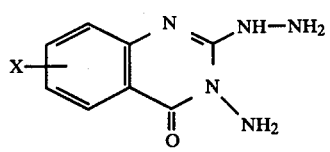

(VI)

wherein X has the above definition with a compound of the formula $$NH_2-(CH_2)_n-OH \qquad (VII)$$

wherein n has the above definition, preferably at elevated temperatures e.g. about 160° C. and the reaction is generally complete in about three days.

The compounds of formula II may alternatively be prepared by reaction of a compound of the formula

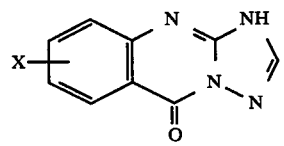

(VIII)

wherein X has the above definition with a compound of the formula $$Hal_1-(CH_2)_n-Hal_2 \qquad (IX)$$

wherein n has the above definition and $Hal_1$ and $Hal_2$ are individually selected from the group consisting of chlorine, bromine and iodine.

Thus, for example, when Hal in the desired compound of formula II is chlorine, the compound of formula IX is preferably a bromo-chloro-alkane wherein one of $Hal_1$ and $Hal_2$ is bromine and the other is chlorine. The reaction is preferably effected in the presence of a base such as sodium hydride or potassium carbonate, potassium carbonate most preferably being used in the presence of a solvent such as acetone at reflux.

[1,2,4]triazolo [5,1-b]quinazolin-5(1H)-one (formula VIII where X is hydrogen) has been described in J. Chem. Soc. Perkin II 1979, 420. The remaining compounds of formula VIII are, however, novel compounds which constitute a further feature of the invention.

The compounds of formula VIII may be obtained by treatment of a compound of the formula

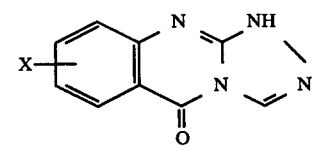

(X)

wherein X has the above definition with an alkaline agent such as an alkali metal hydroxide e.g. sodium or potassium hydroxide, preferably 0.5 M sodium hydroxide solution.

The compounds of formula X are still further novel compounds which form another feature of the present invention. They may be prepared by reacting a compound of the formula

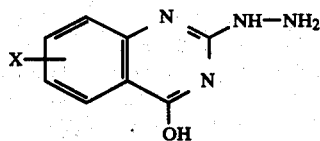

wherein X has the above definition with a formylating agent whereby the desired compound of formula X is obtained. A preferred formylating agent is dimethylformamide and a halide of a weak carboxylic acid, for example an acid having a $pk_a$ greater than or equal to 4 such as an acetyl halide or benzoyl halide, e.g. benzoyl chloride. In this case, the reaction is preferably effected at reflux. When X is nitro, then the formylating agent is preferably trimethyl orthoformate. Other formylating agents may also be used provided that they do not enter into side reactions with other parts of the molecule.

The compounds of formula VI, when they are not known, may be prepared by racting hydrazine hydrate with a 2-alkoxy-3-alkyl-quinazolin-4(3H)-one obtained as described in U.S. Pat. No. 3,755,582. The compound of formula XI wherein X is nitro may be obtained by reacting hydrazine hydrate under mild conditions with a solution of 2-chloro-4-hydroxy-quinazoline previously treated with a sulfo-nitrating mixture. The remaining compounds of formula XI may be obtained by treating an appropriate 2-chloro-4(3H)-quinazolinone described for example, by Hess [J. Med. Chem. January 1968, Vol. 11, p 135] under mild conditions with hydrazine hydrate. The compounds of formula III wherein $R_1$ and $R_2$, together with the nitrogen atom to which they are attached form a piperazino ring substituted with cycloalkyl of 3 to 6 carbon atoms may be prepared by reacting 1-benzylpiperazine with a halide of the appropriate cycloalkane followed by removal of the benzyl group, preferably by catalytic hydrogenation.

The novel antihistaminic and bronchospasmolytic compositions of the invention are comprised of an antihistaminically and bronchospasmolytically effective amount of at least one compound of formula I and their non-toxic, pharmaceutically acceptable acid addition salts and an inert pharmaceutical carrier or excipient. The compositions may be in the form of tablets, dragees, gelatin capsules, granules, aerosols, suppositories or solutions or suspensions, especially the injectable ones.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and/or preservatives.

Due to the antihistaminic and bronchospasmolytic activity, the compositions of the invention are useful for the treatment of asthma, bronchitis and allergic disorders.

The novel method of the invention for treating asthma, bronchitis and allergic disorders in warm-blooded animals, including humans, comprises administering to warm-blooded animals an amount of at least one compound of formula I or its non-toxic, pharmaceutically acceptable acid addition salts in an amount sufficient to treat asthma, bronchitis or allergic disorders.

The active compounds may be administered orally, rectally, parenterally or topically to the skin or mucous. The average daily dose will vary depending upon the condition being treated, the specific compound and the method of administration but the daily dose may be 0.02 to 20 mg/kg.

In the following examples there are described several preferred embodiments to illustrate the invention. However, it should be understood that the invention is not intended to be limited to the specific embodiments.

EXAMPLE 1

1-{4-[4-(m-chlorophenyl)-piperazin-1-yl]-butyl}-triazolo-[1,2,4][5,1-b]-quinazolin-5(1H)-one dihydrochloride STEP A: 3-amino-2-hydrazinoquinazolin-4(3H)-one 3-methyl-2-thioquinazolin-4(3H)-one [described in German OLS No. 2,539,396], 2-chloro 4-hydroxyquinazoline (J. Chem. Soc. (1947), 775) or 2-hydrazino-4-hydroxy-quinazoline [Bull. Soc. Chem. Belg., Vol. 68 (1959), p. 220] was stirred in 5 volumes of hydrazine hydrate at reflux until evolution of amine had ceased (about 5 hours). The mixture was allowed to cool a little and diluted with 5 volumes of water. The mixture was then cooled to room temperature and was filtered. The recovered product was washed with water and then with methanol and dried to obtain a yield of 70–75% of 3-amino-2-hydrazoquinazolin-4(3H)-one.

STEP B: 3-amino-2-(4-hydroxybutylamino)-quinazolin-4(3H)-one 16 g of 3-amino-2-hydrazinoquinazolin-4(3H)-one were stirred in 48 ml of 4-aminobutanol at 160° C. for 3 days and the majority of the 4-aminobutanol was then distilled off under vacuum. The residue was diluted with water and the mixture was seeded and stored at 0° C. overnight to crystallize the product. The mixture was filtered and the recovered product was washed and dried to obtain 12.05 g of 3-amino-2-(4-hydroxybutylamino)-quinazolin-4(3H)-one.

STEP C: 1-(4-hydroxybutyl)-triazolo [1,2,4][5,1-b]-quinazolin-5(1H)-one

A mixture of 23 g of 3-amino-(4-hydroxybutylamino)-4(3H)-one, 15 g of dimethylformamide dimethyl acetal and 2 g of p-toluenesulfonic acid in 230 ml of dry toluene was refluxed until evolution of dimethylamine ceased (about 8 h). The product crystallized on cooling and the mixture was filtered. The recovered product was washed with ether and dried to obtain 22.8 g of 1-(4-hydroxybutyl)-triazolo [1,2,4][5,1-b]-quinazolin-5(1H)-one.

STEP D: 1-(4-chlorobutyl)-triazolo [1,2,4][5,1-b]-quinazolin-5(1H)-one 23 g of the compound of Step B were stirred with 13.5 ml of thionyl chloride in 500 ml of dry dichloroethane at reflux for 6½ hours, whereupon thin-layer chromatography showed the reaction to be complete. The mixture was cooled and stirred with an equal volume of aqueous sodium carbonate until the solid material dissolved. The organic layer was separated, dried over magnesium sulfate and was concentrated to 100 ml whereupon product started to crystallize out. 100 ml of ether were added thereto and the mixture was cooled and filtered. The product was washed with ether and dried to obtain 22.5 g of 1-(4-chlorobutyl)-triazolo [1,2,4][5,1-b]-quinazolin-5(1H)-one.

STEP E:
1-{4-[4-(m-chlorophenyl)-piperazin-1-yl]-butyl}-triazolo [1,2,4][5,1-b]-quinazolin-5(1H)-one-dihydrochloride A mixture of 23 g of the chloro compound of Step C and 25 g of 1-(m-chlorophenyl)-piperazine in 400 ml of dimethylformamide was heated at 110° C. for 15 hours, and was cooled and diluted with 1.5 liters of chloroform. The chloroform solution was washed three times with water, dried over magnesium sulfate and evaporated to dryness under reduced pressure. The residue was dissolved in methanol and the solution was treated with a solution of hydrogen chloride in ethyl acetate to precipitate the hydrochloride salt of the product. The mixture was then filtered and the product was washed with methanol and added to one liter of refluxing methanol. The mixture was cooled and filtered to obtain 31.5 g of 1-{4-[4-(m-chlorophenyl)-piperazin-1-yl]-butyl}-triazolo [1,2,4][5,1-b]-quinazolin-5(1H)-one dihydrochloride.

EXAMPLE 1A
3-amino-2-hydrazino-quinazolin-4 (3H)-one

STEP A: Quinazoline-2,4-dione 978 g of isatoic acid anhydride were added in portions with stirring at 150° C. to a mixture of 720 g of urea and 1 liter of dimethylformamide and the mixture was then heated at 180° C. until evolution of ammonia ceased. The mixture was cooled and one liter of water was immediately added thereto followed by the addition of one liter of methanol. The warm mixture was stirred for one hour and was then filtered. The product was rinsed with warm water and with methanol and was then added with stirring to 2-3 volumes of warm dimethylformamide. The mixture was filtered and the product was rinsed with methanol to obtain 747 g of quinazoline-2,4-dione.

STEP B: 2-chloro-4-hydroxy-quinazoline

A mixture of 300 g of the product of Step A, 150 ml of N,N-dimethyl-aniline and 1 liter of phosphoryl chloride was refluxed for 5½ hours and was cooled and poured with vigorous stirring onto crushed ice. The mixture was filtered and the product was washed with ice water until the wash water was neutral. The product was added with stirring to 2.25 liters of 2 N aqueous sodium hydroxide and the mixture was stirred for about 3 hours until complete dissolution occured. The mixture was filtered and the filtrate was neutralized by addition of glacial acetic acid. The mixture was filtered and the product was washed with water and dried to obtain 263 g of 2-chloro-4-hydroxy-quinazoline.

STEP C: 3-amino-2-hydrazino-quinazolin-4(3H)-one

A mixture of 134 g of the product of Step B and 670 ml of hydrazine hydrate was refluxed with stirring for about 5 hours until evolution of ammonia ceased and the mixture was cooled slightly and was diluted with 670 ml of water. The mixture was cooled to room temperature and was filtered and the product was rinsed with water and methanol and dried to obtain 101.5 of 3-amino-2-hydrazino-quinazolin-4(3H)-one.

EXAMPLE 2
1-{4-[4-(m-chlorophenyl)-piperazin-1-yl]-butyl}-triazolo[1,2,4][5,1-b]-quinazolin-5(1H)-one dihydrochloride

STEP A: Triazolo [1,2,4][3,4-b]-quinazolin-5(1H)-one 10 g of 2-hydrazino-4-hydroxyquinazoline were added to a stirred solution of 20 g of benzoyl chloride in 40 ml of dimethylformamide and the mixture was refluxed until a clear solution was obtained. The solution was poured into water and the mixture was filtered. The product was washed with water and methanol and dried to obtain 8 g of triazolo [1,2,4][3,4-b]-quinazolin-5(1H)-one.

STEP B: Triazolo [1,2,4][5,1-b]-quinazolin-5(1H)-one

The triazolo [1,2,4][3,4-b]-quinazolin-5(1H)-one of Step A was stirred at 90° C. in one mole of 0.5 N aqueous sodium hydroxide until thin-layer chromatography showed the reaction to be complete. The solution was cooled and then acidified with acetic acid and was filtered. The product was washed with water and methanol and dried to obtain a 100% yield of triazolo [1,2,4][5,1-b]-quinazolin-5(1H)-one.

STEP C: 1-(4-chlorobutyl) [1,2,4]-triazolo-[5,1-b]-quinazolin-5(1H)-one

The [1,2,4] triazolo [5,1-b]-quinazolin-5(1H)-one of Step B was alkylated with 4-bromochlorobutane using either sodium hydride/dimethylformamide or refluxing acetone/potassium carbonate. In both cases, a mixture of 1- and 3-substituted products was obtained which were separated on an alumina column. The 3-isomer was eluted with 1-1 mixture of chloroform and petroleum ether (b.p. 60°-80° C.) and then the 1-isomer with chloroform to obtain a 20-30% yield of 1-(4-chlorobutyl) [1,2,4]-triazolo-[5,1-b]-quinazolin-5(1H)-one.

STEP D:
1-{4-[4-(m-chlorophenyl)-piperazin-1-yl]-butyl}[1,2,4] triazolo [5,1-b]-quinazolin-5(1H)-one dihydrochloride A mixture of 23 g of 1-(4-chlorobutyl)-[1,2,4]-triazolo [5,1-b]-quinazolin-5(1H)-one of Step C and 25 g of 1-m-chlorophenylpiperazine in 400 ml of dimethylformamide was heated at 110° for 15 hours and the mixture was diluted with 1.5 liters of chloroform. The chloroform solution was washed three times with water, dried over magnesium sulfate and was evaporated to dryness under reduced pressure. The residue was dissolved in methanol and the solution was treated with a solution of hydrogen chloride in ethyl acetate to precipitate the hydrochloride salt of the product. The mixture was filtered and the product was washed with methanol and was added to one liter of refluxing methanol. The mixture was cooled and filtered to obtain 31.5 g of 1-{4-[4-(m-chlorophenyl)-piperazin-1-yl]-butyl}-[1,2,4] triazolo [5,1-b]quinazolin-5(1H)-one dihydrochloride.

EXAMPLE 3
1-{4-[4-(ethoxycarbonyl)-piperazin-1-yl]-butyl}-7-methyl[1,2,4] triazolo [5,1-b]-quinazolin-5(1H)-one dihydrochloride

STEP A:
3-amino-2-hydrazino-6-methylquinazolin-4(3H)-one 2-mercapto-3,6-dimethylquinazolin-4(3H)-one, 2-chloro-6-methylquinazolin-4-ol, 2-hydrazino-6-methylquinazolin-4-ol or 2-mercapto-6-methylquinazolin-4-ol was stirred in 5 volumes of hydrazine hydrate at reflux for 24 hours and the mixture was diluted with 5 volumes of water. The mixture was cooled to room temperature and was filtered. The product was washed with water and then methanol and dried to obtain a 95% yield of 3-amino-2-hydrazino-6-methylquinazolin-4(3H)-one.

STEP B:
3-amino-2-(4-hydroxybutylamino)-6-methylquinazolin-4(3H)-one 20 g of 3-amino-2-hydrazino-6-methylquinazolin-4(3H)-one were stirred in 100 ml of 4-aminobutanol at 175° C. for 24 hours and the majority of the 4-aminobutanol was then distilled off under vacuum. The residue was diluted with water to crystallize out the product and the mixture was filtered. The product was washed and dried to obtain 16.2 g of 3-amino-2-(4-hydroxybutylamino)-6-methylquinazolin-4(3H)-one.

STEP C: 1-(4-hydroxybutyl)-7-methyl [1,2,4] triazolo [5,1-b]quinazolin-5(1H)-one A mixture of 15 g of 3-amino-2-(4-hydroxybutylamino)-6-methyl-quinazolin-4(3H)-one, 10 g of dimethylformamide dimethylacetal and 1.5 g of p-toluenesulfonic acid in 250 ml of dry toluene was refluxed until evolution of dimethylamine ceased (about 24h.). The mixture was cooled and was filtered. The product was washed with ether and dried to obtain 14 g of 1-(4-hydroxybutyl)-7-methyl [1,2,4] triazolo [5,1-b]-quinazolin-5(1H)-one.

STEP D: 1,(4-chlorobutyl)-7-methyl [1,2,4] triazolo [5,1-b]quinazolin-5(1H)-one 12 g of the hydroxy compound of Step C were stirred with 12 ml of thionyl chloride in 500 ml of chloroform at reflux for 20 hours whereupon thin-layer chromatography showed the reaction to be complete. The hot mixture was stirred with an equal volume of aqueous sodium carbonate until all solid material dissolved out. The organic layer was separated, dried over magnesium sulfate and evaporated to dryness. The residue was washed with ether and dried to obtain 8.8 g of 1-(4-chlorobutyl)-7-methyl-[1,2,4] triazolo-[5,1-b]-quinazolin-5(1H)-one.

STEP E:
1-{4-[4-ethoxycarbonyl-piperazin-1-yl]butyl}-7-methyl [1,2,4] triazolo-[5,1-b]quinazolin-5(1H)-one dihydrochloride A mixture of 8 g of the chloro compound of Step D and 8 g of ethyl piperazine-1-carboxylate in 20 ml of dimethylformamide was heated at 100° C. for 8 hours and the mixture was diluted with 50 ml of chloroform. The chloroform solution was washed three times with water, dried over magnesium sulfate and was evaporated to dryness under reduced pressure. The residue was dissolved in methanol and the solution was treated with 8 ml of concentrated hydrochloric acid to precipitate the hydrochloride salt. The mixture was filtered and the product was washed with methanol and dried to obtain 7.6 g of 1-{4-[4-ethoxycarbonyl-piperazin-1-yl]butyl}-7-methyl [1,2,4] triazolo [5,1-b] quinazolin-5(1H)-one dihydrochloride.

EXAMPLE 4 to 42

Using a method analogous to Example 1, the products indicated in the following Table were prepared and 2-hydrazino-4-hydroxy-6-nitro-quinazoline was prepared according to the following method.

STEP A: 2-chloro-4-hydroxy-6-nitro-quinazoline

A cooled mixture of 70 ml of concentrated sulfuric acid and 35 ml of concentrated nitric acid was added dropwise to a cooled, stirred solution of 90 g of 2-chloro-4-hydroxyquinazoline [J. Chem. Soc., 1947, p. 775] in 270 ml of concentrated sulfuric acid at a rate such that the temperature remained at 5°–10° C. Stirring was continued until the reaction mixture reached room temperature, whereupon it was poured into crushed ice. The 2-chloro-4-hydroxy-6-nitro-quinazoline thus precipitated is filtered off, washed well with water and used directly in the next step.

STEP B: 2-hydrazino-4-hydroxy-6-nitro-quinazoline

The wet product from Step A was dissolved in a mixture of 90 ml hydrazine hydrate and 900 ml of water and the mixture was stirred at 90°–100° C. until crystallization took place. The mixture was allowed to cool and was filtered. The product was washed with water and methanol and dried to obtain 97.2 g of 2-hydrazino-4-hydroxy-6-nitro-quinazoline in the form of a high melting, orange crystalline solid.

| Example | X | n | $-N\begin{smallmatrix}R_1\\R_2\end{smallmatrix}$ | Formula |
|---|---|---|---|---|
| 1,2 | H | 4 | 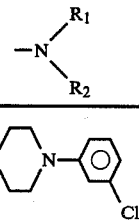 | $C_{23}H_{25}N_6OCl$, 2HCl, $H_2O$ |
| 3 | 7-Me | 4 | 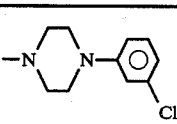 | $C_{21}H_{28}N_6O_3$ 2HCl, $\frac{1}{2}H_2O$ |
| 4 | H | 4 | 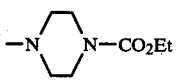 | $C_{24}H_{27}N_5O_2$, 2HCl, $H_2O$ |

-continued

| Example | X | n | -N(R1)(R2) | Formula |
|---|---|---|---|---|
| 5 | H | 4 | 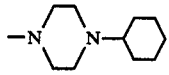 N-methylpiperazine-N-cyclohexyl | $C_{23}H_{32}N_6O \cdot 2HCl$ |
| 6 | H | 3 | 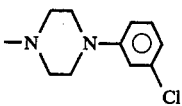 piperazine-3-chlorophenyl | $C_{22}H_{23}N_6OCl,$ $2HCl, 2H_2O$ |
| 7 | H | 3 |  piperidine | $C_{17}H_{21}N_5O,$ $2HCl, \frac{1}{2}H_2O$ |
| 8 | H | 3 | 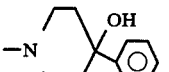 4-hydroxy-4-phenylpiperidine | $C_{23}H_{25}N_5O_2,$ $2HCl$ |
| 9 | H | 3 | 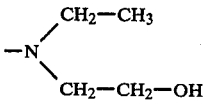 -N(CH2CH3)(CH2CH2OH) | $C_{16}H_{21}N_5O_2,$ $2HCl, \frac{1}{2}H_2O$ |
| 10 | 7-NO2 | 4 | 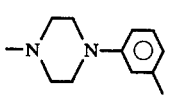 piperazine-3-chlorophenyl | $C_{23}H_{24}N_7O_3Cl$ |
| 11 | H | 5 | 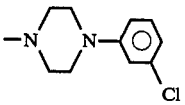 piperazine-3-chlorophenyl | $C_{24}H_{27}N_6OCl,$ $2HCl, 1.\frac{1}{2}H_2O$ |
| 12 | H | 5 |  piperidine | $C_{19}H_{25}N_5O,$ $2HCl, 1.\frac{1}{2}H_2O$ |
| 13 | 7-NO2 | 3 | 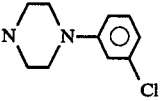 piperazine-3-chlorophenyl | $C_{22}H_{22}N_7O_3Cl, HCl$ |
| 14 | H | 3 | 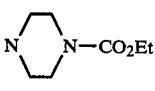 N-CO2Et piperazine | $C_{19}H_{24}N_6O_3$ $2HCl \cdot H_2O$ |
| 15 | H | 4 | 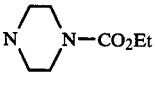 N-CO2Et piperazine | $C_{20}H_{26}N_6O_3$ $2HCl \cdot H_2O$ |
| 16 | H | 4 | 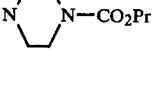 N-CO2Pr piperazine | $C_{21}H_{28}N_6O_2$ $2HCl, \frac{1}{2}H_2O$ |
| 17 | H | 4 | 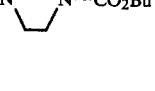 N-CO2Bu piperazine | $C_{22}H_{30}N_6O_3$ $2HCl, \frac{1}{2}H_2O$ |

-continued

| Example | X | n | -N(R1)(R2) | Formula |
|---|---|---|---|---|
| 18 | H | 4 | piperazine-N-CO$_2$isoBu | $C_{22}H_{30}N_6O_3$ 2HCl, ½H$_2$O |
| 19 | H | 4 | piperazine-N-Me | $C_{18}H_{24}N_6O$ 2HCl, 2H$_2$O |
| 20 | H | 4 | piperazine-N-CH$_2$CH$_2$OH | $C_{19}H_{26}N_6O_2$ 3HCl, ½H$_2$O |
| 21 | H | 4 | piperazine-N-CHO | $C_{18}H_{22}N_6O_2$ 2HCl |
| 22 | H | 4 | piperazine-NH | $C_{17}H_{22}N_6O$ 2HCl |
| 23 | 7-Me | 4 | piperazine-N-(3-chlorophenyl) | $C_{24}H_{27}N_6OCl$ 2HCl, H$_2$O |
| 24 | H | 4 | piperidine | $C_{18}H_{23}N_5O$, 2HCl, H$_2$O |
| 25 | 7-Me | 4 | piperazine-N-CO$_2$Pr | $C_{22}H_{30}N_6O_3$ 2HCl |
| 26 | 7-Me | 4 | piperazine-N-CO$_2$isoBu | $C_{23}H_{32}N_6O_3$ 2HCl, ½H$_2$O |
| 27 | 7-Me | 4 | piperazine-N-Me | $C_{19}H_{26}N_6O$ 3HCl, 1.½H$_2$O |
| 28 | 7-Me | 4 | piperazine-N-CH$_2$CH$_2$OH | $C_{20}H_{28}N_6O_2$ 3HCl, ½H$_2$O |
| 29 | 7-Me | 4 | piperazine-N-CHO | $C_{19}H_{24}N_6O_2$ |
| 30 | 7-Me | 4 | piperazine-NH | $C_{18}H_{24}N_6O$ 3HCl, H$_2$O |
| 31 | 7-Me | 4 | piperazine-N-COCH$_3$ | $C_{20}H_{26}N_6O_2$ 2HCl, 1.½H$_2$O |
| 32 | 8-Cl | 4 | piperazine-N-(chlorophenyl) | $C_{23}H_{24}N_6OCl$ 2HCl |

-continued

| Example | X | n | R₁, R₂ (−N<R₁,R₂) | Formula |
|---------|------|---|---|---|
| 33 | 8-Cl | 4 | 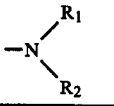 N-CO₂Et | $C_{20}H_{25}N_6O_3Cl$ HCl, ½H₂O |
| 34 | 7-Me | 3 | 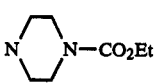 N-CO₂Et | $C_{20}H_{26}N_6O_3$ 2HCl |
| 35 | H | 4 | 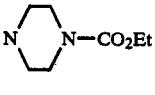 N-CONEt₂ | $C_{22}H_{31}N_7O_2$ 2HCl, H₂O |
| 36 | H | 4 | 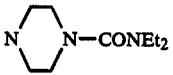 N-CONHMe | $C_{19}H_{25}N_7O_2$ 2HCl |
| 37 | H | 4 | 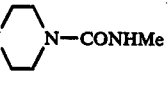 N-CONHEt | $C_{20}H_{27}N_7O_2$ |
| 38 | H | 4 | 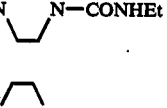 N-CS NHMe | $C_{19}H_{25}N_7OS$ 2HCl, ½H₂O |
| 39 | H | 4 | 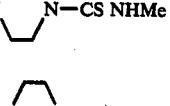 N-SO₂Me | $C_{18}H_{24}N_6O_3S$ 2HCl |
| 40 | H | 4 | 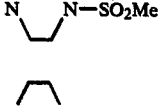 N-CO₂Me | $C_{19}H_{24}N_6O_3$ 2HCl |
| 41 | 7-Me | 4 | 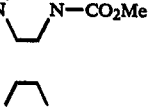 N-CO₂Me | $C_{20}H_{26}N_6O_3$ 2HCl, ½H₂O |
| 42 | H | 4 | 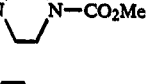 N-⟨⟩-Cl | $C_{23}H_{25}N_6OCl$ 3HCl, ½H₂O |

The analysis data and melting points of the products from the foregoing Table are reported in the following Table.

| Examples | Analysis Calculated/Found | | | | M.P. °C. | Recrystallisation Solvent |
|---|---|---|---|---|---|---|
| | C % | H % | Cl % | N % | | |
| 1,2 | 52.33 | 5.57 | 19.67 | 15.92 | 222–5° | methanol |
| | 52.2 | 5.5 | 19.7 | 15.9 | | |
| 3 | 51.01 | 6.32 | | 17.00 | 228–30° | |
| | 50.6 | 6.3 | | 16.9 | | |
| 4 | | 6.15 | 13.95 | 13.77 | 221–3° | ethyl acetate/ methanol |
| | | 6.1 | 13.8 | 13.9 | | |
| 5 | | | | | 223–5° | |
| 6 | 49.68 | 5.45 | 20.00 | 15.79 | 237–8° | ethanol |
| | 49.3 | 5.4 | 19.6 | 15.7 | | |
| 7 | 51.91 | 6.10 | 18.03 | 17.80 | 245–7° | ethyl acetate/ methanol |
| | 51.9 | 6.0 | | 17.8 | | |
| 8 | 57.99 | 5.71 | 14.88 | 14.70 | 210° | ethyl acetate/ methanol |
| | 57.7 | 5.8 | | 14.7 | | |
| 9 | 48.36 | 6.08 | 17.84 | 17.62 | 170–5° | ethyl acetate/ methanol |
| | 48.3 | 5.6 | | 17.6 | | |
| 10 | | | | | 186–9° | |
| 11 | 52.32 | 5.86 | 19.30 | 15.25 | 226–8 | ethyl acetate/ methanol |
| | 52.3 | 5.9 | 18.5 | 15.5 | | |
| 12 | 51.93 | 6.88 | 16.14 | 15.94 | 216–8° | ethyl acetate/ methanol |
| | 52.0 | 6.7 | 15.4 | 16.3 | | |
| 13 | 52.39 | 4.59 | 14.06 | 19.44 | 275° | |
| | 52.3 | 4.5 | 14.1 | 19.1 | (decomp) | |
| 14 | 48.01 | 5.94 | 14.92 | 17.68 | 222–4° | |
| | 47.9 | 5.6 | 14.5 | 17.6 | (decomp) | |
| 15 | 49.07 | 6.19 | 14.49 | 17.17 | 234–5° | |
| | 49.0 | 5.8 | 14.5 | 17.1 | (decomp) | |
| 16 | 51.02 | 6.32 | 14.34 | 17.00 | 230–2° | ethyl acetate/ methanol |
| | 51.0 | 6.3 | 14.2 | 17.0 | (decomp) | |
| 17 | 51.97 | 6.54 | 13.95 | 16.53 | 230–2° | ethyl acetate/ methanol |
| | 51.6 | 6.6 | 13.5 | 16.5 | (decomp) | |
| 18 | 51.97 | 6.54 | 13.95 | 16.53 | 230–2° | ethyl acetate/ methanol |
| | 52.2 | 6.5 | 14.0 | 16.7 | (decomp) | |
| 19 | 48.11 | 6.73 | 15.78 | 18.70 | 235–7° | |
| | 47.6 | 6.6 | | 15.9 | 18.4 | |
| 20 | 46.68 | 6.19 | 21.76 | 17.19 | 235–7° | |
| | 46.3 | 5.9 | 21.1 | 17.0 | | |
| 21 | | | | | 218–20° (decomp) | |
| 22 | | | | | 220–2° | ethyl acetate/ |

-continued

| | | | | | (decomp) | methanol |
|---|---|---|---|---|---|---|
| 23 | 53.48 | 5.25 | 19.73 | 15.60 | 216–9° | |
| | 53.5 | 5.7 | 19.0 | 15.9 | | |
| 24 | 51.93 | 6.53 | 17.03 | 16.82 | 231–5° | ethyl acetate/ |
| | 52.0 | 6.0 | 16.2 | 17.1 | | methanol |
| 26 | 52.87 | 6.70 | 13.60 | 16.09 | 244–6° | ethyl acetate/ |
| | 52.9 | 6.5 | 13.3 | 16.1 | | methanol |
| 27 | 46.50 | 6.57 | | 17.12 | 240–2° | |
| | 46.9 | 6.5 | | 17.4 | | |
| 28 | 47.77 | 6.42 | | 16.71 | 244–6° | |
| | 47.7 | 6.1 | | 16.7 | | |
| 29 | 61.21 | 6.58 | | 22.55 | 225–7° | (Analysis for free |
| | 61.0 | 6.5 | | 22.5 | | base) |
| 30 | 46.20 | 6.26 | | 17.97 | 250–3° | |
| | 46.1 | 6.3 | | 18.0 | | |
| 31 | 50.00 | 6.04 | | 17.50 | 227.30° | ethyl acetate/ |
| | 50.1 | 5.9 | | 17.6 | | methanol |
| 32 | 50.74 | 4.78 | 26.10 | 15.44 | 235–7° | |
| | 50.5 | 4.8 | 26.1 | 15.5 | | |
| 33 | 50.25 | 5.69 | | 17.57 | 233–5° | |
| | 50.7 | 5.7 | | 17.6 | | |
| 34 | 50.96 | 6.00 | 15.04 | 17.83 | 226–8° | ethyl acetate/ |
| | 50.9 | 6.0 | 15.0 | 17.9 | (decomp) | methanol |
| 35 | 51.16 | 6.83 | 13.73 | 18.98 | 226–7° | |
| | 51.2 | 6.4 | 14.5 | 19.2 | (decomp) | |
| 36 | | | | | 203–5° | |
| | | | | | (decomp) | |
| 37 | 49.18 | 6.40 | | 20.07 | 212–5° | |
| | 48.9 | 6.3 | | 20.0 | (decomp) | |
| 38 | 47.40 | 5.86 | 14.73 | 20.37 | 185–7° | |
| | 47.1 | 5.6 | 15.1 | 19.9 | (decomp) | |
| 39 | 42.86 | 5.79 | 14.06 | 16.66 | 220–2° | (Analysis for +1½ |
| | 43.0 | 5.7 | 14.1 | 16.9 | (decomp) | H₂O) ethyl acetate |
| | | | | | | /methanol |
| 40 | | | | | 215° | |
| | | | | | (decomp) | |
| 41 | 50.00 | 6.04 | | 17.50 | 222–5° | ethyl acetate/ |
| | 50.1 | 5.9 | | 17.6 | | methanol |
| 42 | 50.02 | 5.23 | 25.67 | 15.22 | 230–1° | |
| | 50.2 | 5.2 | 25.4 | 15.4 | (decomp) | |

EXAMPLE 43

Tablets were prepared containing either 15 mg 1-{4-[4-(ethoxycarbonyl)-piperazin-1-yl]-butyl}-7-methyl-[1,2,4]triazolo [5,1-b]-quinazolin-5(1H)-one dihydrochloride or 25 mg of 1-{4-[4-(ethoxycarbonyl)-piperazin-1-yl]-butyl}-7-methyl[1,2,4]triazolo[5,1-b]quinazolin-5(1H)-one dihydrochloride and sufficient excipient of lactose, starch, talc and magnesium stearate for a final weight of 100 mg.

A dosed aerosol was prepared delivering per dose: 2 mg of 1-{4-[4-(ethoxycarbonyl)-piperazin-1-yl]-butyl}-7-methyl-[1,2,4]triazolo[5,1-b]quinazolin-5(1H)-one dihydrochloride, 0.15 mg of emulsifier and 50 mg of propellant.

A syrup was prepared containing 0.3 g of 1-{4-[4-ethoxycarbonyl)-piperazin-1-yl]-butyl}-7-methyl-[1,2,4]triazolo[5,1-b]quinazolin-5(1H)-one and sufficient odoring and sweetening excipient for a final volume of 100 ml.

PHARMACEOLOGICAL STUDY

A. Effects on histamine-induced bronchoconstriction in anaesthetised guinea pigs Male guinea pigs weighing 300–400 grams, after overnight starving, were anaesthetised with intraperitoneal administration of 0.7 ml/100 g of urethane. The preparation was as described by Konsett et al [Arch. exp. Path. Pharmakol. 1195 (1940), p. 71] with a ventilatory pump stroke volume varying between 4 to 6 ml of air (adjusted for each animal) at a stroke rate of 80 per minute to maintain a lung inflation pressure of 7.5 cm of H₂O. Blood pressure was measured via a cannula in the right carotid artery connected to a Statham blood pressure transducer and a Devices M₂ recorder. The test compounds were administered via the cannulated left jugular vein and washed in with 0.1 ml of 0.9% w/w sodium chloride in distilled water. The test product was administered immediately before the histamine which was used as the agonist.

Respiratory changes were recorded via a differential transducer connected to an SE 905 transducer/converter which in turn was connected to a Devices M₂ recorder. The results given in Table I show the effective dose of each of the test compounds required to reduce the histamine-induced constriction in lung air volume by 50%.

TABLE I

| Product of Example | $ED_{50}$ in mg/kg |
|---|---|
| 1 & 2 | 0.02 |
| 3 | 0.008 |
| 4 | 0.3 |
| 5 | 0.9 |
| 6 | 0.03 |
| 7 | 0.3 |
| 8 | 2.0 |
| 10 | 0.1 |
| 11 | 0.05 |
| 12 | 1.0 |
| 15 | 0.05 |
| 24 | 0.7 |
| 34 | 0.01 |

From Table I, it can be seen that the products of Examples 1 and 3 were very effective in antagonising the bronchoconstricting activity of histamine.

B Effect on isolated guinea pig tracheas

Guinea pigs were killed by a blow on the back of the neck and the tracheas were excised, cut spirally and suspended in Krebs Henseleit solution at 37° C. and aerated with 95% $O_2$+5% $CO_2$. Histamine was used as the agonist. Table 2 shows the amount of each test compound required to reduce the histamine-induced contraction of the guinea pig trachea by 50%.

TABLE II

| Product of Example | $EC_{50}$ in μg/ml |
|---|---|
| 1 & 2 | 0.1 |
| 4 | 34 |
| 5 | 10.2 |
| 6 | 0.25 |
| 7 | 15 |
| 12 | 16 |
| 24 | 36 |

The product of Examples 1 and 2 was a potent antagonist of histamine induced contractions and its antagonistic effect was very prolonged and could be demonstrated for up to 30 minutes after the compound had been washed out.

Various modifications of the products and processes of the invention may be made without departing from the spirit or scope thereof and it should be understood that the invention is intended to be limited only as defined in the appended claims.

We claim:

1. A compound selected from the group consisting of triazoloquinazolinones of the formula

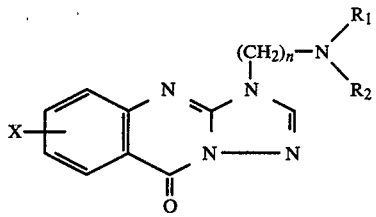

wherein X is selected from the group consisting of hydrogen, halogen, —NO₂, methyl, methoxy and —CF₃, n is an integer from 2 to 5, $R_1$ and $R_2$ are individually selected from the group consisting of hydrogen and alkyl and hydroxyalkyl of 1 to 5 carbon atoms and taken together with the nitrogen atom to which they are attached form a saturated heterocycle selected from the groups consisting of pyrrolidine, piperidino, morpholino and piperazino optionally substituted with at least one member of the group consisting of hydroxy, alkoxy and hydroxyalkyl of 1 to 5 carbon atoms, cycloalkyl of 3 to 6 carbon atoms, acyl of an aliphatic carboxylic acid of 1 to 5 carbon atoms, alkoxycarbonyl of 2 to 6 carbon atoms and phenyl optionally substituted with a halogen or —CF₃ and their non-toxic, pharmaceutically acceptable acid addition salts.

2. A compound of claim 1 wherein X is selected from the group consisting of hydrogen, methyl and nitro, n is 3,4 or 5

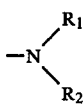

form a saturated heterocycle selected from the group consisting of pyrrolidino, piperidino, morpholino and piperazino optionally substituted with at least one member of the group consisting of hydroxyl, cycloalkyl of 3 to 6 carbon atoms, alkoxycarbonyl of 2 to 6 carbon atoms, phenyl and halophenyl.

3. A compound of claim 2 wherein X is selected from the group consisting of hydrogen and methyl and

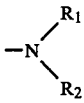

form a heterocycle selected from the group consisting of 4-phenylpiperazin-1-yl, 4-(chlorophenyl)-piperazin-1-yl and 4-(ethoxycarbonyl)-piperazin-1-yl.

4. A compound of claim 1 selected from the group consisting of 1-{4-[4-(m-chlorophenyl)-piperazin-1-yl]-butyl}-[1,2,4] triazolo [5,1-b] quinazolin-5(1H)-one and its non-toxic, pharmaceutically acceptable acid addition salts.

5. A compound of claim 1 selected from the group consisting of 1-{4-[4-(ethoxycarbonyl)-piperazin-1-yl]-butyl}-1,2,4] triazolo [5,1-b] quinazolin-5(1H)-one and its non-toxic, pharmaceutically acceptable acid addition salts.

6. A compound of claim 1 selected from the group consisting of 1-{4-[4-(ethoxycarbonyl)-piperazin-1-yl]-butyl}-7-methyl [1,2,4] triazolo [5,1-b] quinazolin-5(1H)-one and its non-toxic, pharmaceutically acceptable acid addition salts.

7. A compound of claim 1 selected from the group consisting of 1-{3-[4-(ethoxycarbonyl)-piperazin-1-yl]-propyl}-7-methyl [1,2,4]-triazolo [5,1-b] quinazolin-5(1H)-one and its non-toxic, pharmaceutically acceptable acid addition salts.

8. A process for the preparation of a compound of claim 1 comprising reacting a compound of the formula

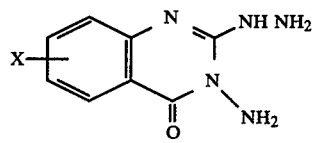

wherein X is as defined in claim 1 with a compound of the formula

NH₂—(CH₂)ₙ—OH wherein n is as defined in claim 1 to obtain a compound of the formula

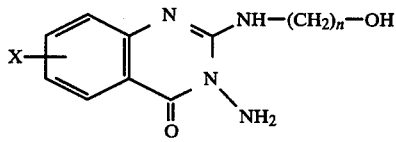

wherein X and n are as defined in claim 1, reacting the latter with a formylating agent to obtain a compound of the formula

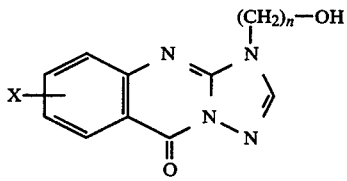

wherein X and n are as defined in claim 1, reacting the latter with a halogenating agent to obtain a compound of the formula

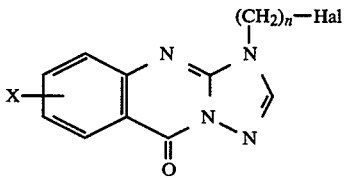

wherein X is as hereinbefore defined and Hal is selected from the group consisting of chlorine, bromine and iodine and reacting the latter with a compound of the formula

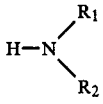

wherein $R_1$ and $R_2$ are as defined in claim 1 to obtain a free base of claim 1 and optionally salifying the latter with a non-toxic, pharmaceutically acceptable acid.

9. A process for the preparation of a compound of claim 1 comprising reacting a compound of the formula

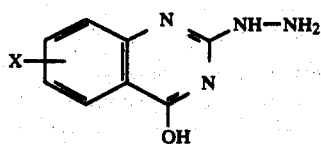

wherein X is as defined in claim 1 with a formylating agent to obtain a compound of the formula

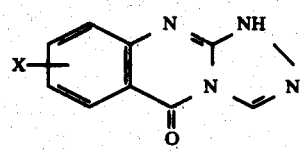

wherein X is as defined in claim 1, reacting the latter with an alkaline agent to obtain a compound of the formula

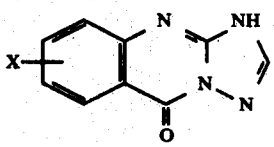

wherein X is as defined in claim 1, reacting the latter with a compound of the formula

Hal$_1$—(CH$_2$)$_n$—Hal$_2$ wherein n is as defined in claim 1 and Hal$_1$ and Hal$_2$ are individually selected from the group consisting of chlorine, bromine and iodine to obtain a compound of the formula

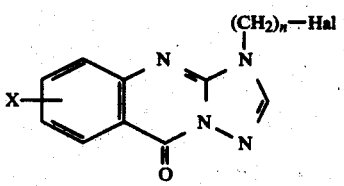

and then reacting the latter with a compound of the formula

wherein R$_1$ and R$_2$ are as defined in claim 1 to obtain the free base of claim 1 and optionally salifying the latter with a non-toxic, pharmaceutically acceptable acid.

10. An antihistaminic and bronchospasmolytic composition comprising an antihistaminically and bronchospasmolytically effective amount of at least one compound of claim 1 and an inert pharmaceutical carrier.

11. A composition of claim 10 wherein X is selected from the group consisting of hydrogen, methyl and nitro, n is 3,4 or 5 and

form a saturated heterocycle selected from the group consisting of pyrrolidino, piperidino, morpholino and piperazino optionally substituted with at least one member of the group consisting of hydroxy, cycloalkyl of 3 to 6 carbon atoms, alkoxycarbonyl of 2 to 6 carbon atoms, phenyl and halophenyl.

12. A composition of claim 10 wherein X is selected from the group consisting of hydrogen and methyl and

form a heterocycle selected from the group consisting of 4-phenylpiperazin-1-yl, 4-(chlorophenyl)-piperazin-1-yl and 4-(ethoxycarbonyl)-piperazin-1-yl.

13. A composition of claim 10 wherein the compound is selected from the group consisting of 1-{4-[4-(m-chlorophenyl)-piperazin-1-yl]-butyl}-[1,2,4] triazolo [5,1-b] quinazolin-5(1H)-one and its non-toxic, pharmaceutically acceptable acid addition salts.

14. A composition of claim 10 wherein the compound is selected from the group consisting of 1-{4-[4-(ethoxycarbonyl)-piperazin-1-yl]-butyl}-[1,2,4] triazolo [5,1-b] quinazolin-5(1H)-one and its non-toxic, pharmaceutically acceptable acid addition salts.

15. A composition of claim 10 wherein the compound is selected from the group consisting of 1-{4-[4-(ethoxycarbonyl)-piperazin-1-yl]-butyl}-7-methyl [1,2,4] triazolo [5,1-b] quinazolin-5(1H)-one and its non-toxic, pharmaceutically acceptable acid addition salts.

16. A composition of claim 10 wherein the compound is selected from the group consisting of 1-{3-[4-(ethoxycarbonyl)-piperazin-1-yl]-propyl}-7-methyl [1,2,4] triazolo [5,1-b] quinazolin-5(1H)-one and its non-toxic, pharmaceutically acceptable acid addition salts.

17. A method of treating asthma, bronchitis and allergic disorders in warm-blooded animals comprising administering to warm-blooded animals an amount of at least one compound of claim 1 sufficient to treat asthma, bronchitis and allergic disorders.

18. A method of claim 17 wherein X is selected from the group consisting of hydrogen, methyl and nitro, n is 3,4 or 5 and

form a saturated heterocycle selected from the group consisting of pyrrolidino, piperidino, morpholino and piperazino optionally substituted with at least one member of the group consisting of hydroxy, cycloalkyl of 3 to 6 carbon atoms, alkoxycarbonyl of 2 to 6 carbon atoms, phenyl and halophenyl.

19. A method of claim 17 wherein X is selected from the group consisting of hydrogen and methyl and

form a heterocycle selected from the group consisting of 4-phenylpiperazin-1-yl, 4-(chlorophenyl)-piperazin-1-yl and 4-(ethoxycarbonyl)-piperazin-1-yl.

20. A method of claim 17 wherein the compound is selected from the group consisting of 1-{4-[4-m-chlorophenyl)-piperazin-1-yl]-butyl}-[1,2,4] triazolo [5,1-b] quinazolin-5(1H)-one and its non-toxic, pharmaceutically acceptable acid addition salts.

21. A method of claim 17 wherein the compound is selected from the group consisting of 1-{4-[4-(ethoxycarbonyl)-piperazin-1-yl]-butyl}-[1,2,4] triazolo [5,1-b] quinazolin-5(1H)-one and its non-toxic, pharmaceutically acceptable acid addition salts.

22. A method of claim 17 wherein the compound is selected from the group consisting of 1-{4-[4-(ethoxycarbonyl)-piperazin-1-yl]-butyl}-7-methyl [1,2,4] triazolo [5,1-b] quinazolin-5(1H)-one and its non-toxic, pharmaceutically acceptable acid addition salts.

23. A method of claim 17 wherein the compound is selected from the group consisting of 1-{3-[4-ethoxycarbonyl)-piperazin-1-yl]-propyl}-7-methyl [1,2,4] triazolo [5,1-b] quinazolin-5(1H)-one and its non-toxic, pharmaceutically acceptable acid addition salts.

* * * * *